United States Patent
Fu

(10) Patent No.: US 8,440,405 B2
(45) Date of Patent: May 14, 2013

(54) METHODS FOR DETECTING VARIANT NUCLEIC ACIDS BY EXTENSION-DEPENDENT DEGRADATION OF PRIMERS

(75) Inventor: Guoliang Fu, Abingdon (GB)

(73) Assignee: 360 Genomics Limited, Penarth, Cardiff ( * ) Notice: Subject to any disclaimer, the term of this patent is extended or adjusted under 35 U.S.C. 154(b) by 445 days.

(21) Appl. No.: 12/529,203

(22) PCT Filed: Feb. 29, 2008

(86) PCT No.: PCT/GB2008/000699
§ 371 (c)(1),
(2), (4) Date: Mar. 4, 2010

(87) PCT Pub. No.: WO2008/104791
PCT Pub. Date: Sep. 4, 2008

(65) Prior Publication Data
US 2010/0184036 A1 Jul. 22, 2010

(30) Foreign Application Priority Data
Mar. 1, 2007 (GB) .................................. 0703997.7

(51) Int. Cl.
*C12Q 1/68* (2006.01)
*C12P 19/34* (2006.01)

(52) U.S. Cl.
USPC .......................... 435/6.12; 435/91.1; 435/91.2

(58) Field of Classification Search ................ 435/6.12, 435/91.1, 91.2
See application file for complete search history.

(56) References Cited

U.S. PATENT DOCUMENTS

| | | | |
|---|---|---|---|
| 5,487,972 A | 1/1996 | Gelfand et al. |
| 5,723,591 A | 3/1998 | Livak et al. |
| 5,849,497 A | 12/1998 | Steinman |
| 5,891,625 A | 4/1999 | Buchardt et al. |
| 5,972,610 A | 10/1999 | Buchardt et al. |
| 6,174,670 B1 | 1/2001 | Wittwer et al. |
| 6,258,569 B1 | 7/2001 | Livak et al. |
| 6,458,544 B1 | 10/2002 | Miller |
| 7,141,377 B2 | 11/2006 | Gelfand et al. |

(Continued)

FOREIGN PATENT DOCUMENTS

| | | |
|---|---|---|
| EP | 0412883 | 2/1991 |
| EP | WO9961661 | 12/1999 |

(Continued)

OTHER PUBLICATIONS

Seyema, et al., Nucleic Acid Res. 1992, 20: 2493-6; A novel biocker-PCR method for detection of rare mutant alleles in the presence of an excess amount of normal DNA. Uses WT-specific blockers flanked by two amplification primers.

(Continued)

*Primary Examiner* — Kenneth R. Horlick
(74) *Attorney, Agent, or Firm* — Andrus, Sceales, Starke & Sawall, LLP

(57) ABSTRACT

The present invention provides methods and kits for detecting the presence or absence or amount of a target nucleic acid or at least one variant nucleotide in one or more target nucleic acids contained in a sample using appropriate primers. The invention is based on systems whereby there is extension-dependent degradation of the primers in the presence of the target, which degradation leads to a detectable signal.

23 Claims, 7 Drawing Sheets

U.S. PATENT DOCUMENTS

| | | | |
|---|---|---|---|
| 2001/0016323 A1 | 8/2001 | Parkhurst et al. | |
| 2002/0098510 A1 | 7/2002 | Su et al. | |
| 2002/0115080 A1 | 8/2002 | Skouv et al. | |
| 2003/0186314 A1 | 10/2003 | Kambara et al. | |
| 2004/0121374 A1 | 6/2004 | Iwaki et al. | |
| 2004/0146866 A1* | 7/2004 | Fu | 435/6 |
| 2004/0248095 A1 | 12/2004 | Behlke et al. | |
| 2006/0183136 A1 | 8/2006 | Pont-Kingdon et al. | |
| 2007/0207494 A1 | 9/2007 | Guo | |

FOREIGN PATENT DOCUMENTS

| | | |
|---|---|---|
| EP | 1082461 | 3/2001 |
| FR | 2779154 | 12/1999 |
| WO | WO9325706 | 12/1993 |
| WO | WO9818965 | 5/1998 |
| WO | 03/027309 | 4/2003 |
| WO | WO03095680 | 11/2003 |
| WO | 2004/048612 | 6/2004 |
| WO | 2004/065628 | 8/2004 |
| WO | WO2007008997 | 1/2007 |
| WO | WO2007045890 | 4/2007 |
| WO | WO2007106534 | 9/2007 |

OTHER PUBLICATIONS

Persons et al., Methods Mol Biol. 2005; 291; 235-45; Allele-specific competitive blocker-PCR detection of rare base substitution. Hybridization of WR-specific blocking primer blocks amplification of WT sequence; mutant templates are preferentially amplified by alle-specific PCR.

Orum, et al., Nucleic Acid Res. 1993, 21; 5332-6; Single base pair mutation analysis by PNA directed PCR clamping, PNAs bind, but they do not prime for extension. Allows selective amplification of target sequences that differ by one base pair.

McKinzie, et al., Mutat Res. 517: 209-20; Detection f rare K-ras cordon 12 mutations using allele-specific competitive blocker PCR, (2002).

Jeffreys, et al, Genome Res, 2003, 13: 2316-2324; DNA enrichment by allele specific hybridization (DEASH): A novel method for haplotyping and for detecting low-frequency base substitutional variants and recombinant DNA molecules.

Holland, P.M. et al., "Detection of specific polymerase chain reaction product by utilizing the 5'-3' exonuclease activity of thermus aquaticus DNA polymerase," Proc. Natl. Acad. Sci. USA (1991) 88:7276-7280.

Salmon, P.M., "Technoscope: La PCR en temps reel," Biofutur (2002) 219:2-8.

International Search Report and Written Opinion for Application No. PCT/GB08/00699 dated Jul. 30, 2008 (13 pages).

International Search Report and Written Opinion for Application No. PCT/GB08/00707 dated Sep. 26, 2008 (18 pages).

* cited by examiner

D

E

SEQUENCE LISTING

```
<160> NUMBER OF SEQ ID NOS: 11

<210> SEQ ID NO 1
<211> LENGTH: 486
<212> TYPE: DNA
<213> ORGANISM: Artificial sequence
<220> FEATURE:
<223> OTHER INFORMATION: Synthetic sequence: BRAF gene fragment

<400> SEQUENCE: 1
ggaaagcatc tcacctcatc ctaacacatt tcaagcccca aaaatcttaa aagcaggtta      60
tataggctaa atagaactaa tcattgtttt agacatactt attgactcta agaggaaaga     120
tgaagtacta tgtttaaag aatattatat tacagaatta tagaaattag atctcttacc     180
taaactcttc ataatgcttg ctctgatagg aaaatgagat ctactgtttt cctttactta     240
```

-continued

```
ctacacctca gatatatttc ttcatgaaga cctcacagta aaaataggtg attttggtct    300
agctacagtg aaatctcgat ggagtgggtc ccatcagttt gaacagttgt ctggatccat    360
tttgtggatg gtaagaattg aggctatttt tccactgatt aaattttggg ccctgagatg    420
ctgctgagtt actagaaagt cattgaaggt ctcaactata gtattttcat agttcccagt    480
attcac                                                                486

<210> SEQ ID NO 2
<211> LENGTH: 27
<212> TYPE: DNA
<213> ORGANISM: Artificial sequence
<220> FEATURE:
<223> OTHER INFORMATION: Synthetic sequence: Primer BrafF2

<400> SEQUENCE: 2
ggaaagcatc tcacctcatc ctaacac                                         27

<210> SEQ ID NO 3
<211> LENGTH: 29
<212> TYPE: DNA
<213> ORGANISM: Artificial sequence
<220> FEATURE:
<223> OTHER INFORMATION: Synthetic sequence: Primer BrafEndR

<400> SEQUENCE: 3
gactttctag taactcagca gcatctcag                                       29

<210> SEQ ID NO 4
<211> LENGTH: 23
<212> TYPE: DNA
<213> ORGANISM: Artificial sequence
<220> FEATURE:
<223> OTHER INFORMATION: Synthetic sequence: Primer BrafFam
<220> FEATURE:
<221> NAME/KEY: misc_feature
<222> LOCATION: (13)..(13)
<223> OTHER INFORMATION: n is dT-Fam
<220> FEATURE:
<221> NAME/KEY: misc_feature
<222> LOCATION: (19)..(19)
<223> OTHER INFORMATION: n is dT-BHQ1

<400> SEQUENCE: 4
ggacccactc cancgagant tca                                             23

<210> SEQ ID NO 5
<211> LENGTH: 49
<212> TYPE: DNA
<213> ORGANISM: Artificial sequence
<220> FEATURE:
<223> OTHER INFORMATION: Synthetic sequence: Primer JKR3ccF2

<400> SEQUENCE: 5
gatgctctga gaaaggcatt agaaagcatc tttattatgg cagagagaa                 49

<210> SEQ ID NO 6
<211> LENGTH: 23
<212> TYPE: DNA
<213> ORGANISM: Artificial sequence
<220> FEATURE:
<223> OTHER INFORMATION: Synthetic sequence: Primer JKR3

<400> SEQUENCE: 6
gatgctctga gaaaggcatt aga                                             23

<210> SEQ ID NO 7
```

```
<211> LENGTH: 27
<212> TYPE: DNA
<213> ORGANISM: Artificial sequence
<220> FEATURE:
<223> OTHER INFORMATION: Synthetic sequence: Primer JKFamdR
<220> FEATURE:
<221> NAME/KEY: misc_feature
<222> LOCATION: (12)..(12)
<223> OTHER INFORMATION: n is BHQ-1(dT)
<220> FEATURE:
<221> NAME/KEY: misc_feature
<222> LOCATION: (24)..(24)
<223> OTHER INFORMATION: n is Fam-dR

<400> SEQUENCE: 7
gttttactta cnctcgtctc cacngaa                                          27

<210> SEQ ID NO 8
<211> LENGTH: 27
<212> TYPE: DNA
<213> ORGANISM: Artificial sequence
<220> FEATURE:
<223> OTHER INFORMATION: Synthetic sequence: Primer JKR3Hex

<400> SEQUENCE: 8
aacagatgct ctgagaaagg cattaga                                          27

<210> SEQ ID NO 9
<211> LENGTH: 20
<212> TYPE: DNA
<213> ORGANISM: Artificial sequence
<220> FEATURE:
<223> OTHER INFORMATION: Synthetic sequence: Primer JKR3Dab

<400> SEQUENCE: 9
cctttctcag agcatctgtt                                                  20

<210> SEQ ID NO 10
<211> LENGTH: 25
<212> TYPE: DNA
<213> ORGANISM: Artificial sequence
<220> FEATURE:
<223> OTHER INFORMATION: Synthetic sequence: Primer JKF7

<400> SEQUENCE: 10
gtatgatgag caagctttct cacaa                                            25

<210> SEQ ID NO 11
<211> LENGTH: 23
<212> TYPE: DNA
<213> ORGANISM: Artificial sequence
<220> FEATURE:
<223> OTHER INFORMATION: Synthetic sequence: Blocking primer BrafFamWTB
<220> FEATURE:
<221> NAME/KEY: misc_feature
<222> LOCATION: 3..4, 4..5, 5..6, 6..7, 7..8, 8..9, 9..10
<223> OTHER INFORMATION: phosphorothioate linkage
<220> FEATURE:
<221> NAME/KEY: misc_feature
<222> LOCATION: 12..13, 13..14, 14..15, 15..16
<223> OTHER INFORMATION: phosphorothioate linkage
<220> FEATURE:
<221> NAME/KEY: misc_feature
<222> LOCATION: (19)..(19)
<223> OTHER INFORMATION: n is dR-biotin
<220> FEATURE:
<221> NAME/KEY: misc_feature
<222> LOCATION: (22)..(23)
<223> OTHER INFORMATION: phosphorothioate linkage
```

```
<400> SEQUENCE: 11
ggacccactc catcgagant tca                              23
```

METHODS FOR DETECTING VARIANT NUCLEIC ACIDS BY EXTENSION-DEPENDENT DEGRADATION OF PRIMERS

CROSS-REFERENCE TO RELATED APPLICATIONS

This patent application is a national stage filing under 35 U.S.C. 371 of International Application No. PCT/GB2008/000699, filed on Feb. 29, 2008, which claims foreign priority benefits to United Kingdom Patent Application No. 0703997.7, filed on Mar. 1, 2007. These applications are incorporated herein by reference in their entireties.

TECHNICAL FIELD

The present invention is directed to methods for detecting and/or quantifying a target nucleic acid or one or more variant nucleotide sequences contained in a test sample.

BACKGROUND OF THE INVENTION

Single nucleotide polymorphisms (SNPs) are the most common type of variation in the human genome. Mutations are also usually SNPs but the term is normally reserved for those with a frequency rarer than 1% or where there is a known functional, disease-causing role for the variation (Gibson N J, 2006, Clin Chim Acta. 363(1-2):32-47). There are many applications for genotyping polymorphisms and detecting rare mutations. The detection of rare variants is important for the early detection of pathological mutations, particularly in cancer. For instance, detection of cancer-associated point mutations in clinical samples can improve the identification of minimal residual disease during chemotherapy and detect the appearance of tumour cells in relapsing patients The measurement of mutation load is also important for the assessment of environmental exposure to mutagens, to monitor endogenous DNA repair, and to study the accumulation of somatic mutations in aging individuals. Additionally, more sensitive and quantitative methods to detect rare variants can revolutionise prenatal diagnosis, enabling the characterisation of foetal cells present in maternal blood. A vast number of methods have been introduced, but no single method has been widely accepted. Many methods for detecting low-frequency variants in genomic DNA use the polymerase chain reaction (PCR) to amplify mutant and wild-type targets. The PCR products are then analysed in a variety of ways, including sequencing, oligonucleotide ligation, restriction digestion, mass spectrometry or hybridization with allele-specific oligonucleotides to identify the variant against the background of wild-type DNA. Other methods use allele-specific PCR to selectively from the low-frequency variant, with or without additional selection. For example, by digesting PCR products with a restriction enzyme that specifically cleaves the wild-type product. Current approaches have inherent limitations due to the lack of total specificity of allele-specific primers during PCR, which creates false positives. As a result, all current approaches have limited sensitivity and accuracy (review in Jeffreys A J and May C A, 2003 Genome Res. 13(10): 2316-24).

The real-time polymerase chain reaction (PCR) can be used for SNP genotyping. It is carried out in a closed-tube format and it is quantitative. Several methods are currently available for performing real-time PCR, such as utilising TaqMan probes (U.S. Pat. Nos. 5,210,015 and 5,487,972, and Lee et al., Nucleic Acids Res. 21:3761-6, 1993), molecular beacons (U.S. Pat. Nos. 5,925,517 and 6,103,476, and Tyagi and Kramer, Nat. Biotechnol. 14:303-8, 1996), self-probing amplicons (scorpions) (U.S. Pat. No. 6,326,145, and Whitcombe et al., Nat. Biotechnol. 17:804-7, 1999), Amplisensor (Chen et al., Appl. Environ. Microbiol. 64:4210-6, 1998), Amplifluor (U.S. Pat. No. 6,117,635, and Nazarenko et al., Nucleic Acids Res. 25:2516-21, 1997, displacement hybridization probes (Li et al., Nucleic Acids Res. 30:E5, 2002); DzyNA-PCR (Todd et al., Clin. Chem. 46:625-30, 2000), fluorescent restriction enzyme detection (Cairns et al. Biochem. Biophys. Res. Commun. 318:684-90, 2004) and adjacent hybridization probes (U.S. Pat. No. 6,174,670 and Wittwer et al., Biotechniques 22:130-1, 134-8, 1997). These methods are generally not suitable for mutation detection due to low accuracy, however.

The unifying problem behind all of these PCR approaches for detecting rare variants is replication infidelity during amplification or impreciseness of probe hybridisation. This is apparent in a popular mutation detection method described by Newton et al (Nucleic Acids Res. 17:2503-16, 1989; U.S. Pat. No. 5,595,890). This system, an amplification refractory mutation system (ARMS), exploits allele-specific primers that are used for a PCR reaction. Mispriming during amplification often yields inaccurate results.

EP0663447 relates to a method of detecting a polynucleotide by hybridizing a polynucleotide of known nucleotide sequence with a nuclease-resistant oligonucleotide primer having a sequence complementary to a part of said polynucleotide, then adding at least one kind of deoxynucleoside triphosphate, DNA polymerase and nuclease thereto, synthesizing a complementary strand being a nucleotide species located adjacent to the 3'-terminal of said primer and complementary to said polynucleotide, followed by decomposition thereof, the synthesis and decomposition of said complementary strand being repeated one or more times, and detecting the resulting pyrophosphoric acid or deoxynucleoside monophosphate Nevertheless, it will be appreciated that the provision of nucleic acid detection methods that are both accurate and sensitive would provide a contribution to the art.

DISCLOSURE OF THE INVENTION

Various aspects of the invention are described in the aspects, embodiments and claims below.

In one aspect the invention provides a method for detecting and/or quantifying a target nucleic acid in a sample (which may be a target sequence including the presence or absence of at least one variant nucleotide), said method comprising:

(a) treating the sample, under hybridising conditions, with a first oligonucleotide primer capable of hybridising to a first region of said target nucleic acid, (b) maintaining the mixture of step (a) under extension conditions (e.g. which may comprise appropriate nucleoside triphosphates and a nucleic acid polymerase) to extend any annealed primer, wherein primer extension is dependent on the presence of the target nucleic acid sequence (e.g. on the presence or absence of a variant nucleotide), (c) maintaining the mixture of step (b) under degradation conditions to degrade the extension product of the first primer, if present, wherein degradation of the first primer extension product including the first primer is dependent on extension of said first primer, and wherein degradation of said first primer extension product generates a detectable signal which is indicative of the presence of the target nucleic acid (e.g. of the variant nucleotide in the target nucleic acid).

Thus the degradation of the first primer extension product degrades at least the first primer portion of the product.

Optionally, the presence or level of detectable signal is correlated with the presence and\or amount of the target nucleic acid sequence or a particular variant nucleotide of the target nucleic acid sequence.

Thus, briefly, the method employs selective degradation of a first primer (within an extension product) which is dependent on the primer having been extended, which in turn is dependent on the presence of the target sequence or the variant nucleotide on the target sequence. The region to which the first primer anneals will generally be a 'diagnostic portion' comprising or adjacent to a suspected variant nucleotide.

It will be understood that "dependent upon" in this context may be quantitative or qualitative. Thus in the absence of the target sequence or a particular variant nucleotide of the target sequence there is no extension of the first primer, but there will be a proportional extension of the first primer in the presence of the target sequence or the suspected nucleotide on the target sequence.

As described below, degradation is preferably achieved via the extension of a second primer upstream of the first primer by a polymerase having 5' to 3' exonuclease activity. This will significantly degrade the first primer extension product (which forms a stable duplex with the target) but may not degrade the annealed, unextended first primer which is dissociated from the template under extension conditions.

As described below, extension is preferably made dependent on the presence of the target nucleic acid by annealing the first primer such that its terminal 3' nucleotide is complementary to a distinctive nucleotide (e.g. variant nucleotide) in the target sequence. Thus, if the distinctive nucleotide in the target sequence is not present, an extension of the first primer will be inhibited or prevented.

All combinations of the various embodiments and claims (including dependent claims) described below apply mutatis mutandis to the aspects of the invention as described above.

DETAILED DESCRIPTION OF THE INVENTION

Figure 1:
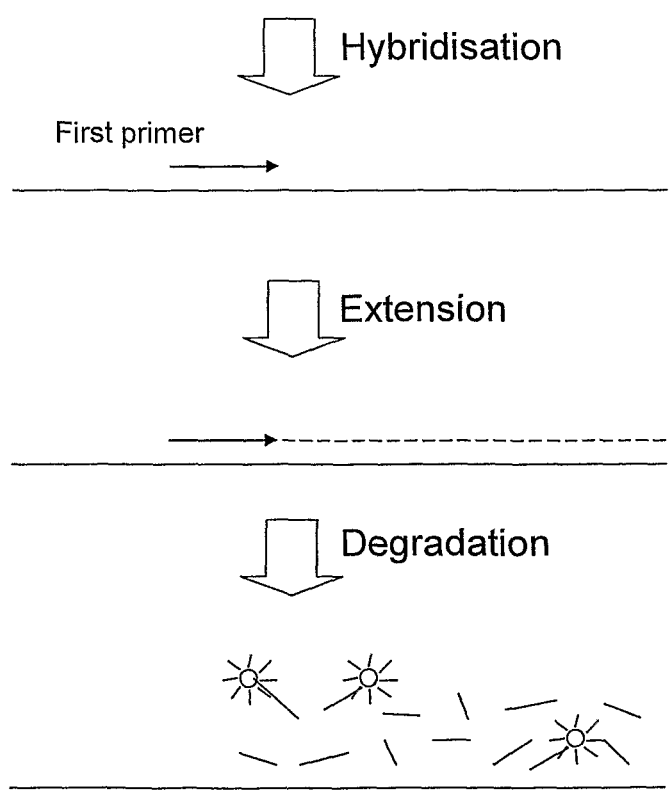
FIG. 1 provides an illustration of the steps and products of a disclosed method, wherein a first primer with a 3' terminal nucleotide being complementary to the corresponding nucleotide on the target sequencer anneals to the diagnostic region (the first region). The annealed first primer is extended on the templates containing the appropriate nucleotides under extension conditions. Under degradation conditions, the extended strand from the first primer is degraded and a detectable signal is generated.
Figure 2:
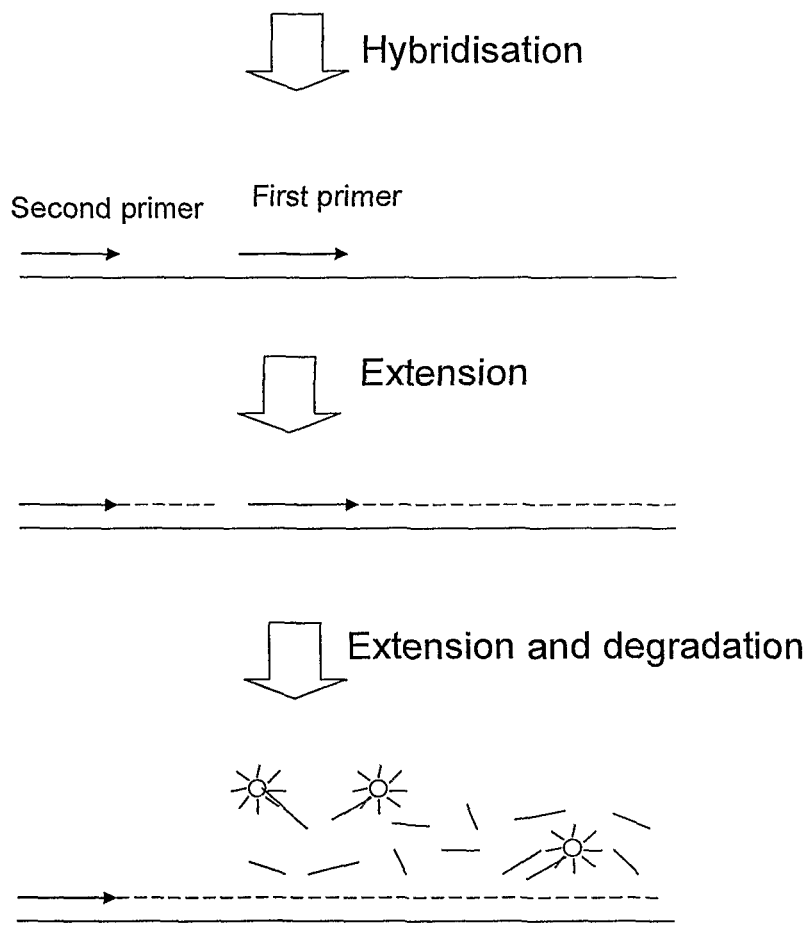
FIG. 2 provides an illustration of another embodiment of the invention, wherein a first primer with a 3' terminal nucleotide being complementary to the corresponding nucleotide on the target sequencer anneals to the diagnostic region (the first region). The second primer anneals to the second region upstream 5' of the first primer. The annealed first and second primers are extended on the templates containing the appropriate nucleotides under extension conditions. Under degradation conditions, the extended strand from the first primer is degraded and a detectable signal is generated.
Figure 3:
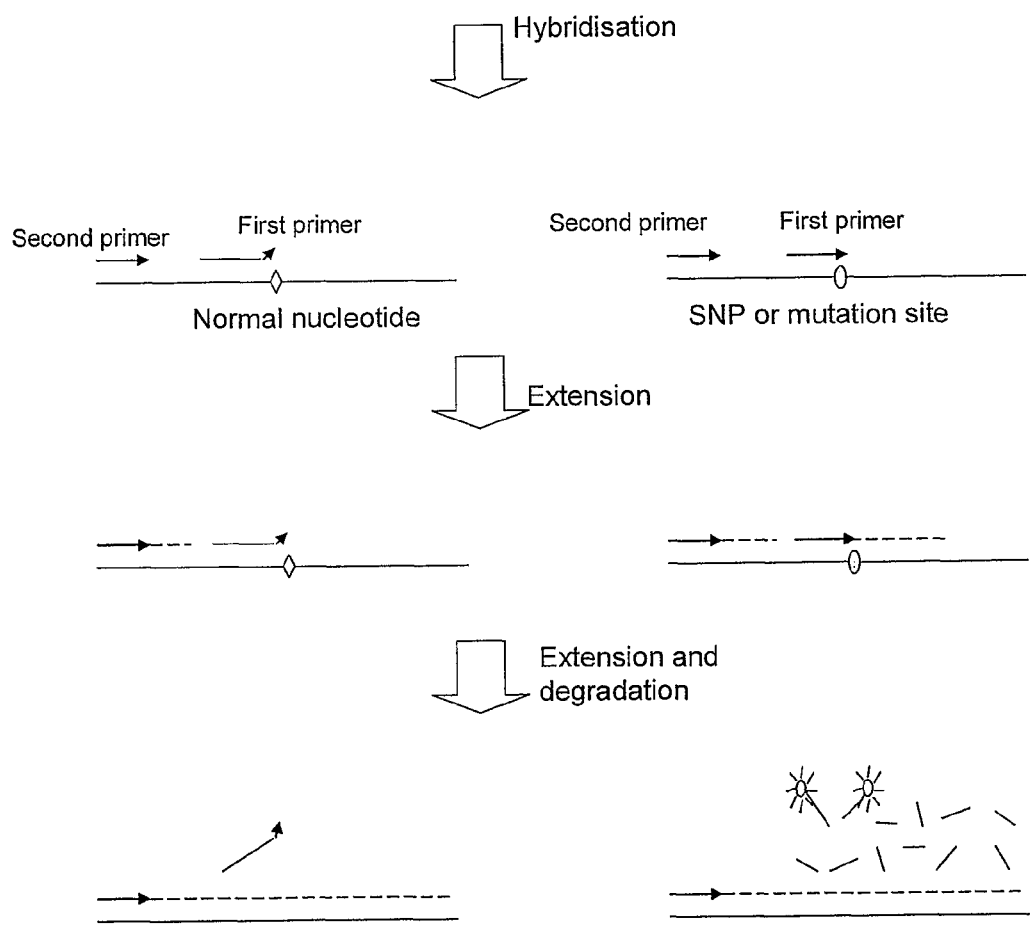
FIG. 3 provides an illustration of a method for detecting a SNP or mutation, wherein a first primer with a 3' terminal nucleotide being complementary to a SNP or mutated nucleotide anneals to the diagnostic region (first region) with normal or variant nucleotides. The second primer anneals to the second region upstream of the first primer. The matched first and second primers are extended on the templates containing the appropriate nucleotides under extension conditions. Under degradation conditions, the extended strand from the first primer including the first primer is degraded and a detectable signal is generated. The mismatched first primer is non-extendable and is dissociated from template and no detectable signal is generated.

The present invention is directed to methods for detecting and\or quantifying a target nucleic acid, detecting the presence or absence of target nucleic acids, or quantifying the amount of one or more variant nucleotides in one or more target nucleic acid sequences. The present invention is of particular interest for the diagnostic detection of mutations in cancer or other diseases, SNP genotyping, and SNP-association testing by allele quantification in DNA pools. It is useful for viral load quantification by designing a control standard nucleic acid containing a variant nucleotide. It is also useful in the detection and typing of infectious pathogens by analysing either their DNA or RNA.

I. Materials

A. Target Nucleic Acid in a Sample

A sample refers to any substance containing or presumed to contain nucleic acid and includes a sample of tissue or fluid isolated from an individual or individuals. As used herein, the terms "nucleic acid", "polynucleotide" and "oligonucleotide" refer to primers, probes, oligomer fragments to be detected, oligomer controls, and unlabeled blocking oligomers, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA. The oligonucleotide is comprised of a sequence of approximately at least 6 nucleotides, preferably of at least about 10-12 nucleotides, and more preferably of at least about 15-20 nucleotides corresponding to a region of the designated nucleotide sequence.

As used herein, the term "target sequence" or "target nucleic acid sequence" refers to a region which is to be either amplified, detected or both. The target sequence, which is the object of amplification and detection, can be any nucleic acid. The target sequence can be RNA, cDNA, genomic DNA, or DNA from a disease-causing microorganism or virus. The target sequence can also be DNA treated by chemical reagents, various enzymes or physical exposure. A target nucleic acid sequence of interest in a sample may appear as single-stranded DNA or RNA such as cDNA, mRNA, other RNA, or as separated complementary strands. Separating complementary strands of target nucleic acid may be accomplished by physical, chemical or enzymatic means.

B. Primers

The term "Primer" as used herein refers to an oligonucleotide, whether occurring naturally or produced synthetically, which is capable of acting as a point of initiation of synthesis when placed under conditions in which synthesis of a primer extension product that is complementary to a nucleic acid strand is induced, i.e., in the presence of nucleotides and an agent for polymerization such as DNA polymerase and at a suitable temperature and buffer. The primer is preferably single-stranded for maximum efficiency in amplification but may alternatively be double-stranded. The primer must be sufficiently long to prime the synthesis of extension products in the presence of the inducing agent. The exact lengths of the primers will depend on many factors including temperature, source of primer and use of the method.

The term "complementary to" is used herein in relation to nucleotides to mean a nucleotide that will base pair with another specific nucleotide. Thus adenosine triphosphate is complementary to uridine triphosphate or thymidine triphosphate and guanosine triphosphate is complementary to cytidine triphosphate. It is appreciated that whilst thymidine triphosphate and guanosine triphosphate may base pair under certain circumstances they are not regarded as complementary for the purposes of this specification. It will also be appreciated that whilst cytosine triphosphate and adenosine triphosphate may base pair under certain circumstances they are not regarded as complementary for the purposes of this specification. The same applies to cytosine triphosphate and uracil triphosphate.

The primers herein are selected to be "substantially" complementary to the different strands of each specific sequence to be replicated. This means that the primers must be sufficiently complementary to hybridize with their respective strands. Therefore, the primer sequence need not reflect the exact sequence of the template. For example, where the first primer comprises a nucleotide sequence in which the 3'-terminal nucleotide is complementary to either the suspected variant nucleotide or the corresponding normal nucleotide, a non-complementary nucleotide fragment may be attached to the 5'-end of the primer, with the remainder of the primer sequence being complementary to the diagnostic portion of the target base sequence. Commonly, however, the primers have exact complementarity except in so far as non-complementary nucleotides may be present at a predetermined primer terminus as herein before described.

It will be appreciated, however, that in certain circumstances synthesis of a primer extension product might be induced to occur even in the presence of a non-complementary 3'-terminal residue. Artefacts may result from an annealing/incubation temperature that is too low (in which case the temperature may be increased), an incubation/annealing time that is too long (in which case the time may be reduced), a salt concentration that is too high (in which case the salt concentration may be reduced), an enzyme or nucleoside triphosphate concentration that is too high, an incorrect pH, or an incorrect length of oligonucleotide primer. Artefactual results may be avoided by deliberately introducing one or more further mismatched residues, or if desired, deletions or insertions, within the diagnostic primer to destabilise the primer by further reducing the binding during hybridisation.

The "first primer" as used herein is a diagnostic primer, referring to the primer which hybridises to the diagnostic region of a target sequence, and is extended if an appropriate nucleotide is present in the target sequence and the first primer (in the extension product thereof) is subsequently degraded. The first primer may have a nucleotide sequence such that a terminal nucleotide thereof is selected to be either complementary to the suspected variant nucleotide or to the corresponding normal nucleotide. An extension product of the first primer may be synthesised when the terminal nucleotide of the first primer is complementary to the appropriate nucleotide of the corresponding diagnostic portion (the first region) of the target nucleic acid sequence, but no such extension product may be synthesised when the terminal nucleotide of the first primer is not complementary to the appropriate nucleotide of the corresponding diagnostic portion (the first region) of the target nucleic acid sequence.

The first primer may also have a nucleotide sequence such that a non-terminal nucleotide thereof is selected to be either complementary to the suspected variant nucleotide or to the corresponding normal nucleotide. An extension product of the first primer may be synthesised when the first primer comprising the non-terminal nucleotide complementary to the suspected variant nucleotide hybridises to the target sequence containing the appropriate nucleotide of the diagnostic portion (the first region) of the target nucleic acid sequence, but no such extension product may be synthesised when the non-terminal nucleotide of the first primer is not complementary to the appropriate nucleotide of the corresponding diagnostic portion (the first region) of the target nucleic acid sequence.

Thus it will be appreciated that where any aspect or claim herein refers to "terminal nucleotide" the invention may be likewise practised with a non-terminal nucleotide which is in sufficient proximity to the terminal nucleotide to achieve the same effect i.e. to permit or prevent extension when the relevant primer is annealed to the diagnostic portion which is complementary or non-complementary respectively. Typically such non-terminal nucleotides would nevertheless be separated by only 1, 2, or 3 nucleotides from the terminus.

It should be appreciated that for a suspected variant nucleotide on the first strand of the target nucleic acid there is a corresponding complementary variant nucleotide on the second strand of the target nucleic acid, which is complementary to the first strand. In the practice of a method of the present invention, one may include one first primer for the first strand of the target sequence in a reaction; alternatively one may include one first primer for the first strand of the target sequence and another first primer for the second strand of the target sequence in a single reaction. In the latter case, one first primer for the first strand of the target sequence has an overlapping (complementary) 3' terminal nucleotide with the first primer for the second strand of the target sequence.

The first primer may be a labelled oligonucleotide. The term "label" as used herein refers to any atom or molecule which can be used to provide a detectable (preferably quantifiable) signal, and which can be attached to a nucleic acid or protein. Labels may provide signals detectable by fluorescence, radioactivity, colourimetry, gravimetry, magnetism, enzymatic activity and the like.

The first primer may be attached to a solid support. Multiple first primers may be arrayed on a solid support. The solid support can include any solid material to which oligonucleotides can be coupled. This includes, but is not limited to, materials such as acrylamide, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfirmerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-support is a glass slide.

Figure 5:
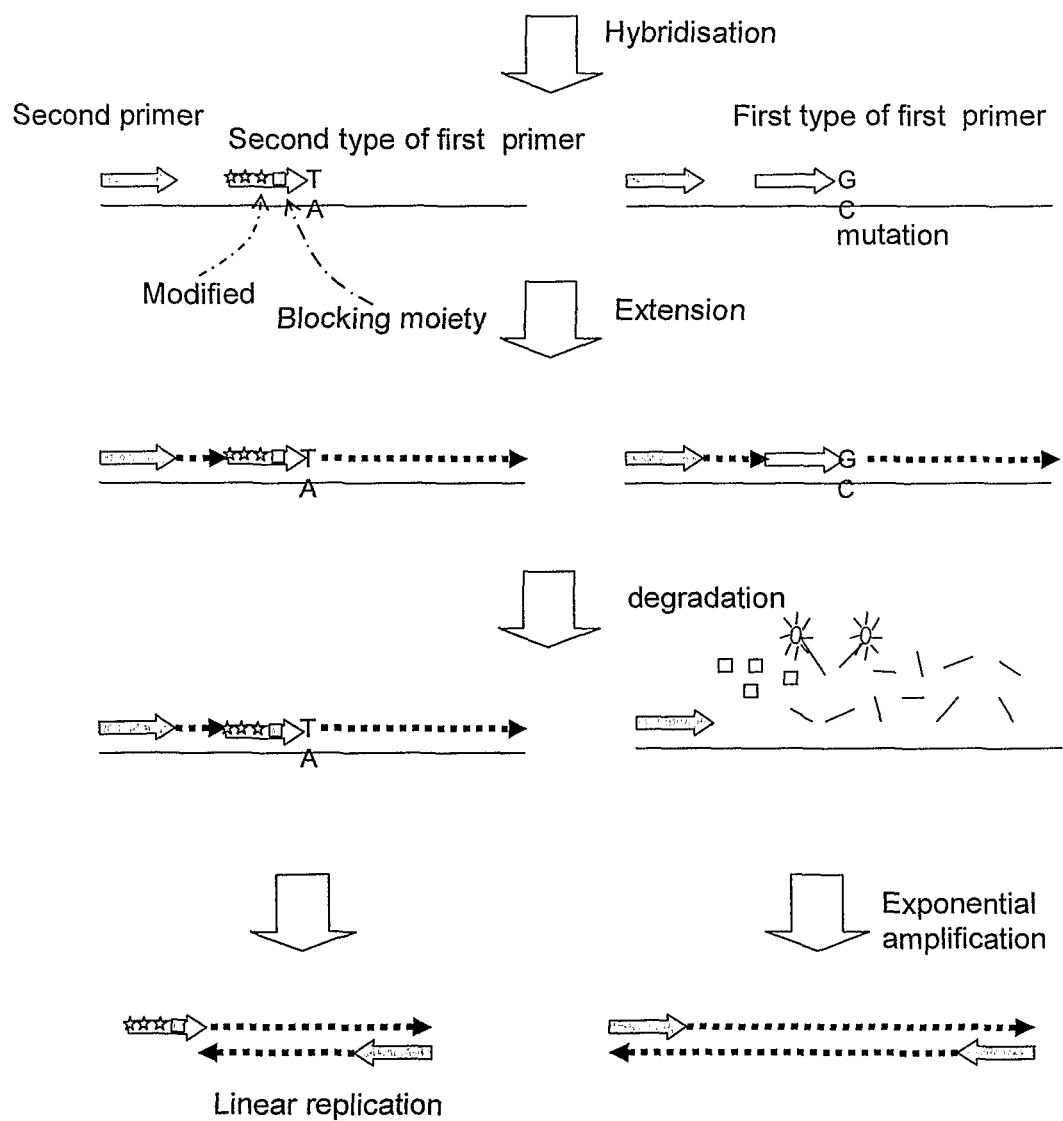
FIG. 5 is a schematic diagram of an embodiment of the present invention, wherein a second type of the first primer with a 3' terminal nucleotide (T, thymidine) being complementary to the corresponding normal nucleotide (A, adenosine) is modified, which renders the whole or part of the first primer resistant to nuclease cleavage. The first type of the first primer with a 3' terminal nucleotide (G, guanine) being complementary to the mutated nucleotide (C, cytidine) is not modified, and is sensitive to nuclease cleavage. The annealed first primers as well as the second primers are extended on the templates containing the appropriate nucleotides under extension conditions. Under degradation conditions, which may be the same conditions as the extension conditions, the extended strand from the first type of the first primer is degraded and a detectable signal is generated. Since a 5' nuclease activity of an enzyme, which may be a DNA polymerase, cannot cleave the second type of the first primer, the extension of the upstream second primer is blocked by the extension product of the second type of the first primer, thereby suppressing amplification of the target sequence containing the normal nucleotide.

In one embodiment, it may be desirable that enrichment and detection of a target sequence of interest are carried out in the same reaction (FIG. 5). The first primer may act as a blocking primer as well as a detecting primer. For the first primer to play a role as a blocking primer, the first primer may comprise modified nucleotides or modified linkages which render the whole or part of the blocking primer resistant to nuclease cleavage. Particularly, the second type of the first primer, with a 3' terminal nucleotide being complementary to the corresponding normal nucleotide, is modified. It is preferred that the last 5 nucleotides or linkages at the 3' end and/or the 5' end are modified such that the first primer is resistant to nuclease cleavage. It is also possible that the last nucleotide or linkage at the 3' end and/or the 5' end is modified such that the blocking primer is resistant to nuclease cleavage. Any type of modification which renders the primer resistant to exonuclease cleavage can be used. Examples include phosphorothioate linkage, methylphosphonate linkage, LNA, PNA, Oligo-2'-OMe-nucleotides, or the like.

The first primer may comprise a moiety that renders the extension product of the first primer unsuitable for an exponential amplification. In one embodiment, the moiety may be a blocking moiety, wherein the replication of all or part of said first primer is blocked, and the primer extension molecule generated from a template of the first primer extension strand is therefore not suitable as a template for a further primer extension, as it lacks a primer binding site. The blocking moiety may be a HEG, non-nucleotide linkage, nucleotides derivatives, or a dye. The blocking moiety may be located at less than 18 nucleotides away from 3' terminus of the first primer. It is preferred that the blocking moiety may be located at less than 6 nucleotides away from 3' terminus of the first primer. It is more preferred that the blocking moiety may be located at less than 3 nucleotides away from 3' terminus of the first primer.

The second primer is capable of hybridizing to the same nucleic acid strand to which the first primer is capable of hybridizing. The portion of the target nucleic acid sequence where the second primer anneals is called the second region. The second region and the first region of the target sequence may be or may not be overlapping The second region is located 3' of the first region. In other words, the first primer and the second primer anneal to the target nucleic acid such that the 3' end of the second primer is adjacent to or upstream of the 5' end of the first primer. When two different, non-overlapping oligonucleotides anneal to different regions of the same linear, complementary nucleic acid sequence, and the 3' end of one oligonucleotide points toward the 5' end of the other, the former may be called the "upstream" oligonucleotide and the latter the "downstream" oligonucleotide. Herein the second primer is an upstream primer.

The third primer is capable of hybridising to the nucleic acid strand complementary to the nucleic acid strand to which the first primer and second primer are capable of hybridising. The second and third primers may each be an amplification primer with a nucleotide sequence such that each is capable of hybridising to the extension product of the other primer after separation from its complement, whereby the first and third primer extension products serve as templates for synthesis of an extension product of the amplification primer, thereby facilitating amplification.

For a given nucleotide variation, for example a point mutation, its presence or absence may be detected either 1) by designing the first primer to have an appropriate terminal nucleotide which is complementary to the suspected nucleotide variation such that the synthesis and degradation of the first primer extension product will be indicative of the presence of the suspected nucleotide variation, and the absence of the synthesis and degradation of the first primer extension product will be indicative of the absence of the suspected nucleotide variation; or 2) by designing the first primer to have an appropriate terminal nucleotide which is complementary to the corresponding normal nucleotide (the other allele) such that the synthesis and degradation of the first primer extension product will be indicative of the presence of the normal nucleotide, and no synthesis of the first primer extension product will be indicative of the absence of the normal nucleotide. In this regard a reference herein to the "appropriate terminal nucleotide" means the terminal nucleotide of the primer from which, in use, synthesis would be initiated if possible. Thus since in general the agent for polymerisation would initiate synthesis at the 3' end of the primer, the appropriate terminal nucleotide would, in general, be the 3' terminal nucleotide.

It is preferred that the first primer in a reaction comprises of two types which are different at the 3' terminal nucleotide and comprise different labels. The first type of the first primer comprises an appropriate terminal nucleotide which is complementary to the suspected nucleotide variation (one allele), whereas the second type of the first primer comprises an appropriate terminal nucleotide which is complementary to the normal nucleotide (the more frequent allele). When one type of first primer anneals to the first region of a target with the appropriate variant nucleotide, the first primer matches to the appropriate region of the target, thereby initiating primer extension. When one type of first primer anneals to the first region of a target where the nucleotide of interest is not complementary to the 3' terminal nucleotide of first primer, this type of first primer mismatches to the appropriate region of the target, thereby primer extension is not initiated. The term "match" or "mismatch" refers to the hybridization potential of paired nucleotides in complementary strands of DNA. Matched nucleotides hybridize efficiently, such as the classical A/T and G/C base pairs.

Of course more than two types of distinctively labelled primer could also be used where desired. In one embodiment, the present invention is directed to detection of the presence, absence, or quantification of more than one suspected variant nucleotide in the same sample. In this case, more than one first primer targeting different SNPs or mutations may be included in a reaction.

Figure 4:
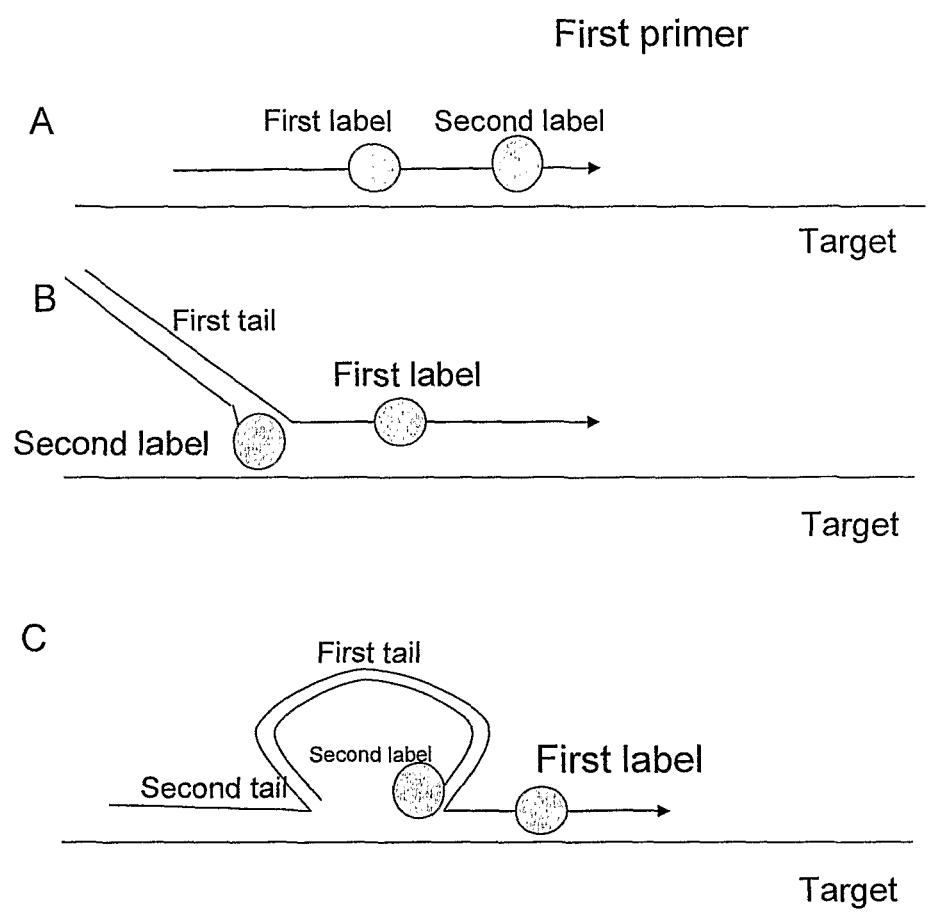
FIG. 4 illustrates various first and second primers annealing to the target nucleic acid sequence. (A) The first primer is labelled with an interactive label pair which are located not at the 5' end. The interactive pair may be a fluorophore and quencher. (B) The first primer comprises a 5' tail which is hybridised with a complement oligonucleotide. The first primer and the complement oligonucleotide are each labelled with one member of the interactive pair. The interactive pair may be a fluorophore and quencher. (C) The first primer comprises, apart from the first 5' tail, a second 5' tail which is capable of hybridising to the target nucleic acid. The first 5' tail is capable of hybridising to a complement oligonucleotide. The first primer and the complement oligonucleotide are each labelled with one member of the interactive pair. The interactive pair may be a fluorophore and quencher. (D) The first primer comprises a region capable of forming a double-stranded duplex with a complement oligonucleotide that is capable of hybridising to the first primer. The first primer hybridises to the target nucleic acid more strongly than it hybridises to the complement oligonucleotide. The first primer and the complement of the first primer are each labelled with one member of a interactive label pair (first label and second label) such that upon hybridization of the first primer with the amplified products the interactive labels are separated. The two labels can be located at any place on the first primer and the complement oligo. (E) The second primer comprises a region capable of forming a double-stranded duplex with a complement oligonucleotide that is capable of hybridising to the second primer. The second primer hybridises more strongly to the target nucleic acid than it hybridises to the complement oligonucleotide. The second primer and the complement of the second primer are each labelled with one member of an interactive label pair (first label and second label) such that upon hybridization of the second primer with the amplified products the interactive labels are separated
Figure 4:
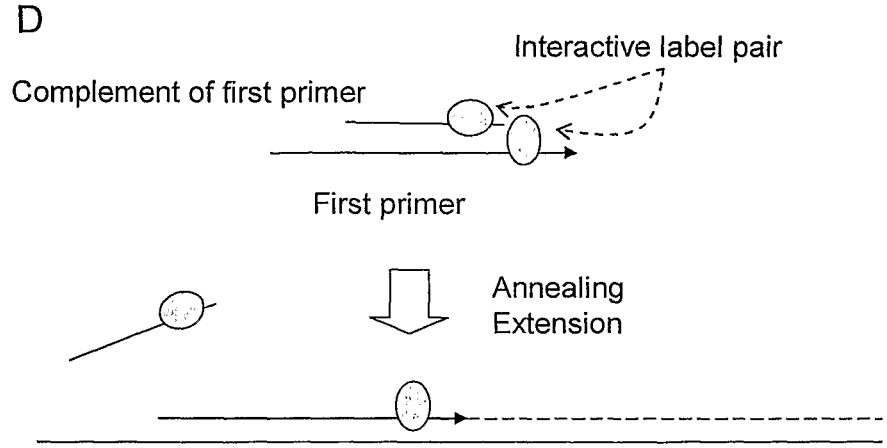
Figure 4:
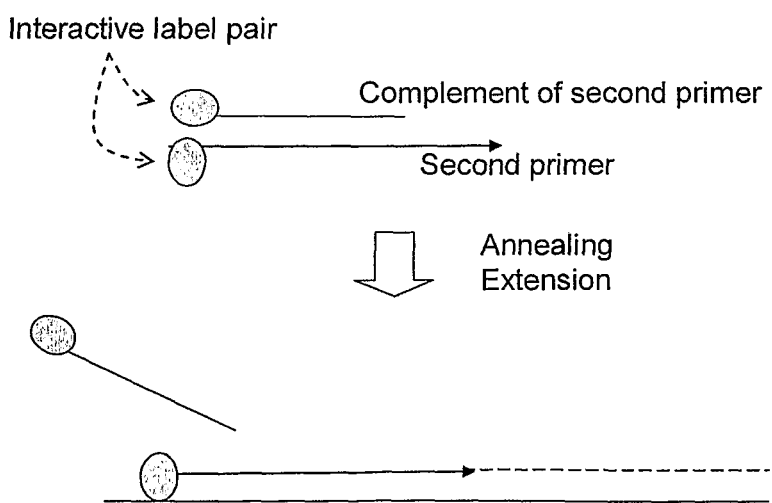

It is preferred that the first primer is labelled (FIG. 4). It is further preferred that the labelling of the first primer is not at the 5' terminus. It is designed so that the first primer extension product is degraded, which generates detectable signals. The first primer may anneal to the target, but if it does not match the appropriate nucleotide, it will not be extended, thereby not generating a detectable signal. Under appropriate extension conditions such as a higher temperature than that used for the primer annealing, the annealed, unextended first primer will be dissociated from template. In some circumstances a hybridization condition, for example a temperature which usually favours the primer annealing, may contain a residual activity of primer extension and degradation. The residual activity of the degradation may cleave a small portion of the annealed first primer, which results in the remainder of the first primer being destabilized and dissociating from the template molecule. As the labels are located at the middle and near the 3' end of the first primer, a detectable signal will not be generated from this annealed, but not extended, first primer. In this regard, it is preferred that the first primer is labelled at least 3 nucleotides away from the 5' terminus. It is further preferred that the first primer is labelled at least 6 nucleotides away from the 5' terminus. It is more preferable that the first primer is labelled at least 9 nucleotides away from the 5' terminus.

The first primer may be comprised of a first label and second label. The first label and second label may be an interactive pair comprising fluorophores or non-fluorophore dyes. One example of such interactive labels is a fluorophore-quencher. The space between the first label and second label is given such that separation of the two labels is permitted during degradation of the extension product.

"Fluorophore" as used herein to refer to moieties that absorb light energy at a defined excitation wavelength and emit light energy at a different defined wavelength. Examples of fluorescence labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Cyanine dyes (Cy3, Cy6, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine 6G, Rhodamine Green, Rhodamine Red, Rhodol Green, 2', 4', 5', 7'-Tetrabromosulfone-fluorescein, Tetramethyl-rhodamine (TMR), Carboxytetramethylrhodamine (TAMRA), Texas Red and Texas Red-X.

As used herein, the term "quencher" includes any moiety that is capable of absorbing the energy of an excited fluorescent label when it is located in close proximity to the fluorescent label and capable of dissipating that energy without the emission of visible light. Examples of quenchers include, but are not limited to, DABCYL (4-(4'-dimethylaminophenylazo)benzoic acid) succinimidyl ester, diarylrhodamine carboxylic acid, succinimidyl ester (QSY-7), and 4',5'-dinitrofluorescein carboxylic acid, succinirnidyl ester (QSY-33), quencherl, or "Black hole quenchers" (BHQ-1, BHQ-2 and BHQ-3).

The first primer for use in the disclosed methods in the present invention comprises a 3' sequence complementary to a target sequence, which is normally used for priming an extension reaction. This part of the primer is referred to as the 3' priming portion of the first primer. The first primer may comprise additional sequences 5' of the priming portion of the first primer that may or may not be complementary to a target sequence; this additional sequence is referred to as a tail. In one embodiment, the first primer comprises a first tail which is not complementary to a target sequence. The first tail may comprise non-nucleic acids or a sequence of nucleotides. The first tail may be double-stranded, wherein an oligonucleotide complementary to the first tail anneals to the first tail sequence. It is preferred that the first primer is labelled with a first label at the non-tail sequence, wherein the complement oligonucleotide to the first tail is labelled with second label at the 5' terminus or near the 5' terminus (FIG. 4B). Again, the first label and second label may be interactive fluorophores or non-fluorophore dyes as defined above.

In another embodiment, the first primer may further comprise a second tail of non-nucleic acids or a sequence of nucleotides that is linked to the first tail and is substantially complementary to the target nucleic acid sequence. The second tail may comprise a sequence which is capable of annealing to the adjacent region 3' to the region to which the priming portion of the first primer is capable of annealing (FIG. 4C).

The first primer may comprise a region capable of forming double stranded duplex with a complement oligonucleotide which is capable of hybridising to the first primer. The first primer hybridises more strongly to the target nucleic acid than it hybridises to the complement oligonucleotide. The first primer and the complement oligo of the first primer are each labelled with one member of an interactive label pair (first label and second label) such that upon hybridization of the first primer with the amplified products the first and second labels are separated. It is preferred that the complement oligonucleotide is blocked at the 3' end. The labels can be located at any positions on the first primer and the complement oligonucleotide. Preferably, a label may not be located at the 5' end of the first primer (FIG. 4D).

The second primer may comprise a region capable of forming double stranded duplex with a complement oligonucleotide which is capable of hybridising to the second primer. The second primer hybridises more strongly to the target nucleic acid than it hybridises to the complement oligonucleotide. The second primer and the complement oligonucleotide of the second primer are each labelled with one member of a interactive label pair (first label and second label) such that upon hybridization of the second primer with the amplified products the first and second labels are separated. The labels can be located at any positions on the second primer and the complement oligonucleotide. A label may be located at the 5' end of the second primer (FIG. 4E)

B. Nucleoside Triphosphate

The term "nucleoside triphosphate" is used herein to refer to nucleosides present in either DNA or RNA and thus includes nucleosides which incorporate adenine, cytosine, guanine, thymine and uracil as a base, the sugar moiety being deoxyribose or ribose. In general deoxyribonucleosides will be employed in combination with a DNA polymerase. It will be appreciated, however, that other modified bases capable of base pairing with one of the conventional bases adenine, cytosine, guanine, thymine and uracil may be employed. Such modified bases include for example 8-azaguanine and hypoxanthine.

The term "nucleotide" as used herein can refer to nucleotides present in either DNA or RNA and thus includes nucleotides which incorporate adenine, cytosine, guanine, thymine and uracil as a base, the sugar moiety being deoxyribose or ribose. It will be appreciated however that other modified bases capable of base pairing with one of the conventional bases adenine, cytosine, guanine, thymine and uracil may be used in the primers employed in the present invention. Such modified bases include for example 8-azaguanine and hypoxanthine.

It will be appreciated that where the process of the present invention is to be used for detecting the presence or absence of a suspected variant nucleotide that is adjacent to a portion of the target base sequence, which does not contain all four different nucleotides, then an extension product of the first primer and, if desired, an extension product of other primers may be formed in the presence of only the appropriate corresponding nucleoside triphosphates and all four different nucleoside triphosphates would not be necessary.

In one embodiment, at least one of the nucleoside triphosphates is labelled, whereby degrading the extension product of the first primer generates detectable signals. Examples of labelled nucleotides include, but not limited to, AMCA-dUTP, Biotin-dUTP, Digoxigenin-dUTP, TMR-dUTP, Fluorescein-dUTP, Rho-green-X-dUTP, Cy5-dCTP and TR770-dATP.

C. Enzyme

The disclosed methods make use of a nucleic acid polymerase for primer extension and a nuclease activity for degradation of the primer extension product. It is preferred that the nuclease activity is an exonuclease activity. It is most preferable that the exonuclease activity is a 5' to 3' exonuclease activity. Suitable enzymes for providing such nuclease activity include, for example, Lambda Exonuclease, T7 exonuclease Taq DNA polymerase and *E. coli* DNA polymerase amongst other enzymes. Any nucleic acid polymerase can be used. It is preferred that primer extension and degradation is provided by the same enzyme, for which Taq DNA polymerase is a candidate. It is also preferred that the same enzyme can also be used for amplification. It is particularly preferable that the DNA polymerase is a thermostable DNA polymerase.

II Method

The disclosed methods involve an extension of the first primer annealed to a target nucleic acid template and subsequent degradation of the extension product of the first primer, thereby generating detectable signals. The key factor of this method is the capability to extend the annealed first primer, which determines whether detectable signals can be generated. For various reasons, the annealed first primer on the target template may not be extendable, for example if the 3' terminus nucleotide of the first primer is not complementary to the variant (or normal) nucleotide on the target to which the first primer anneals. Thus, two types of the first primer can be designed with the first type of the first primer specific for the variant nucleotide and second type of the first primer specific for the normal nucleotide. Both types of the first primer may be labelled differently, whereby the accurate typing of different alleles, or the presence or absence of a particular nucleotide can be obtained.

This invention differs from a previously described method in U.S. Pat. No. 5,487,972. Firstly, the U.S. Pat. No. 5,487,972 method uses probe hybridization as the only means for signal generation, wherein the probe anneals to the target and generates a signal. It may be expected that the probe can anneal inappropriately, thereby generating a false signal. Therefore, the U.S. Pat. No. 5,487,972 method may be unsuitable for accurately detecting rare mutations or the quantification of a variant nucleotide in a target sequence. In contrast the method of the present invention uses the power of accurate polymerisation of the first primer, wherein primer extension is a necessity for generating detection and quantification signals. In the methods of this invention, unlike the method described in U.S. Pat. No. 5,487,972, the primer/probe is designed such that it does not generate a detection signal upon hybridisation to the target sequence. Secondly, the U.S. Pat. No. 5,487,972 method uses probes labelled at the 5' terminus, whereas the primer used in the present invention is preferably not labelled at the 5' terminus. As outlined above, in the U.S. Pat. No. 5,487,972 method signal generation correlates with probe hybridisation. The current method exploits a completely different approach wherein the simple annealing of a probe (primer) will not generate detection signals; instead the occurrence of extension of the first primer is necessary to generate a detection signal. The lack of a label at the 5' terminus of the first primer eliminates the generation of false signals from residual activity of the degradation of annealed, unextended first primer. Thirdly, the U.S. Pat. No. 5,487,972 method uses a probe that is blocked at the 3' end, whereas the method of the present invention uses a primer that is extendable. Fourthly, the correct ratio (i.e. quantitative data) between variant target nucleic acids and normal nucleic acids can be obtained in the method of the present invention, whereas the U.S. Pat. No. 5,487,972 method cannot obtain such a quantitative data. Finally, the method of the present invention can use labelled nucleoside triphosphates that incorporate into the primer extension product and generate detection signals upon degradation of the primer extension product.

One method of the invention is provided for detecting a target nucleic acid or the presence or absence of at least one variant nucleotide in one or more target nucleic acids contained in a test sample from an individual, with reference to a control or controls, said method comprising:

(a) treating the sample with a first oligonucleotide primer for a first region of a target nucleic acid sequence to create a mixture of duplexes comprising the first oligonucleotide primer annealed to the target nucleic acid under hybridisation conditions, wherein the nucleotide sequence of said first primer is such that it is substantially complementary to said first region of the target nucleic acid, wherein said first region comprises a suspected variant nucleotide;

(b) maintaining the mixture of step (a) under extension conditions, which comprise appropriate nucleoside triphosphates and a nucleic acid polymerase, to extend the annealed first primer, if extendable, to synthesize an extension product of the first primer; and (c) degrading the first primer extension product (including the first primer), if present, under degradation conditions, thereby generating detectable signals which are indicative of the presence of the target nucleic acid or the variant nucleotide in the target nucleic acid, or the level of detectable signal is correlated with the amount of the target nucleic acid sequence or a particular variant nucleotide on the target nucleic acid sequence.

The first oligonucleotide primer anneals to a target nucleic acid to form a mixture of duplexes under hybridisation conditions, which comprise appropriate buffer and temperature. When in step (b) the annealed first primer is not extended under extension conditions, no extension product of the first primer is generated. Consequently, in step (c) no degradation of the extension product of the first primer occurs under degradation conditions, therefore no detectable signals are generated, which is indicative of the absence of the target nucleic acid or particular variant nucleotide in the target nucleic acid. When in step (b) a portion of the annealed first primers is extended under extension conditions. The portion of extended first primers is correlated with the amount of the particular nucleotide present in the target sequence. The particular nucleotide may be a SNP or a mutated nucleotide(s). The first primer may comprise a 3' terminus nucleotide complementary to the SNP or mutated nucleotide. Consequently, in step (c) the degradation of the extension product of the first primer occurs under degradation conditions, therefore detectable signals are generated, which are indicative of the amount of the target nucleic acid or particular variant nucleotide in the target nucleic acid.

It is preferred that degrading the extension product of the first primer occurs in a template-dependent manner. Many enzymes can cleave the primer extension product in a template-dependent manner, for example T7 exonuclease or the 5' to 3' nuclease activity of Taq DNA polymerase. It is preferred that the enzymes providing primer extension and degrading are the same enzyme, for example Taq DNA polymerase.

In another embodiment, the step (a) comprises treating the sample with a first oligonucleotide primer for a first region of a target nucleic acid sequence and a second oligonucleotide primer for a second region of the same strand of target nucleic acid sequence to create a mixture of duplexes comprising the first and second oligonucleotide primers annealed to the target nucleic acid under hybridisation conditions, wherein the nucleotide sequence of the first primer is such that it is substantially complementary to the first region of the target nucleic acid, the nucleotide sequence of said second primer is such that it is substantially complementary to said second region of the target nucleic acid, and wherein the duplexes comprise the target nucleic acid annealed to the first primer and to the second primer such that the 3' end of the second primer is adjacent to or upstream of the 5' end of the first primer, in other words, the second region of the target nucleic acid is located 5' of the first region of the target nucleic acid.

In this embodiment, step (b) further comprises extending the annealed first and second primer, if extendable; to synthesize extension products of the first and second primers under extension conditions, which comprise appropriate nucleoside triphosphates and a nucleic acid polymerase, and in step (c) the degrading of the extension product of the first primer occurs during extension of the second primer.

In another embodiment, step (a) further comprises treating the sample with at least two types of the first oligonucleotide primer for a first region of a target nucleic acid sequence to create a mixture of duplexes comprising the first oligonucleotide primer annealed to the target nucleic acid under hybridising conditions. The nucleotide sequence of the first primer is such that it is substantially complementary to the first region of the target nucleic acid, a 3' terminal nucleotide of the first type of the first primer being complementary to a suspected variant nucleotide, and a 3' terminal nucleotide of the second type of the first primer being complementary to the corresponding normal nucleotide. In step (b) an extension product of the first type of the first primer is synthesized when the first type of the first primer anneals to the first region containing the suspected variant nucleotide in the target nucleic acid sequence, no extension product being synthesized when the first type of the first primer anneals to the first region containing the corresponding normal nucleotide in the target nucleic acid. An extension product of the second type of the first primer is synthesized when the second type of the first primer anneals to the first region containing the normal nucleotide in the target nucleic acid sequence, no extension product being synthesized when the second type of the first primer anneals to the first region containing corresponding variant nucleotide in the target nucleic acid.

If the second type of the first primer comprises modified nucleotides or linkages which render the second type of the first primer resistant to nuclease cleavage, the second type of the first primer may play a role as a blocking primer. When the modified second type of the first primer anneals to the first region containing the normal nucleotide in the target nucleic acid sequence, an extension product is synthesized. Since the 5' nuclease activity of an enzyme cannot cleave the second type of the first primer, the extension of the upstream second primer is blocked by the extension product of the second type of the first primer, thereby suppressing an amplification of the target sequence containing the normal nucleotide. Consequently, the reaction enriches the target sequence containing the variant nucleotide.

In a preferred embodiment, the steps (a), (b) and (c) are parts of a PCR reaction, which comprises:

i) treating the sample under denaturing conditions to separate the primer extension product from its template, where such an extension product is formed;

ii) contacting single strands produced above, either together or sequentially, with appropriate nucleoside triphosphates, a nucleic acid polymerase, a first primer (or two types of a first primer), a second primer and a third primer whereby, where possible, further extension products are synthesized using the single strands produced above as a template, wherein degradation of the extension product of the first primer, employing said nucleic acid polymerase having 5' to 3' nuclease activity, occurs during extension of the second primer, and wherein said third primer comprises a sequence substantially complementary to the extension product of the second primer;

iii) repeating the above steps a sufficient number of times to result in detectable changes of the detection labels.

It should be appreciated that the PCR reaction described above may comprise one first primer for a first strand of the target sequence and another first primer for the second strand of the target sequence which is complementary to the first strand of the target sequence. Using first primers for both strands of the target sequence may increase the detection signal and the specificity.

In either method described herein, a sample is provided which is suspected of containing the target nucleic acid or the particular nucleotide variant of interest. The target nucleic acid contained in the sample may be double-stranded genomic DNA, or cDNA if necessary, which is then denatured using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for a length of time ranging from a few seconds to minutes. As an alternative to denaturation, the target nucleic acid may exist in a single-stranded form in the sample, for example single-stranded RNA or DNA viruses.

The denatured nucleic acid strands are then incubated with oligonucleotide primers which may include first primer, second primer or third primer under hybridization conditions: conditions which enable the binding of the primers to the single nucleic acid strands. The first primer extension product is subsequently degraded, thereby not serving as a template, whereas the second and third primers are selected so that their relative positions along a duplex sequence are such that an extension product synthesized from one primer, when separated from its template (complement), serves as a template for the extension of the other primer. In theory the first primer extension product may be completely degraded. In reality there is likely to be some leakage whereby a small fraction of the first primer extension product is not degraded and incorporated into a double stranded fragment. This leakage does not, however, adversely affect the accuracy of the present invention.

Likewise it will be appreciated that although the present invention is based on extension-dependent degradation, whereby (for example) no significant degradation of the extension product of the first primer occurs under degradation conditions, and thereby no detectable signals are generated in practice, nevertheless some de minimis degradation of even unextended primer may in principle occur. However such does not adversely affect the accuracy of the present invention.

In the practice of the invention, the first primer must be first or simultaneously annealed to a complementary nucleic acid before the second primer extension blocks the first primer binding site. To achieve this, a variety of techniques may be employed. One can position the first primer so that the 5' end of the first primer is relatively far from the 3' end of the second primer, thereby giving the first primer more time to anneal. One can also use a first primer having a higher melting temperature than the second primer. Melting temperature (Tm) by definition is the temperature at which one half of the DNA duplex will dissociate to become single-stranded and indicates the duplex stability. For example, the first primer can be designed to be longer than the second primer. The nucleotide composition of the first primer can be chosen to have greater G/C content and, consequently, greater thermal stability than the second primer. In a similar fashion, one can incorporate into the first primer modified nucleotides which contain base analogs that form more stable base pairs than the bases typically present in naturally occurring nucleic acids.

The thermocycling parameters can also be varied to take advantage of the differential thermal stability of the two types of first primers, and the second and third primers. For example, following the denaturation step in thermocycling, an intermediate temperature may be introduced which is permissible for first primer binding but not second and third primer binding, and then increased to extension temperature (for example 72° C.), thereby permitting extension of the matched first primer and the melting away of mismatched first primer. The cycles of an intermediate temperature and extension temperature can be repeated as many times as is desirable to allow the matched first primer extension on as many target templates as possible. The temperature can then be reduced to permit second and third primer annealing and extension.

Since the first primer extension product should not be used as a template for replication, a blocking moiety incorporated in the first primer that will block replication of part or whole of the first primer can be used. In principle, the blocking moiety included in the first primer may be any entity which is not recognized as suitable template by a polymerase.

Template-dependent extension of the oligonucleotide primer(s) is catalyzed by a polymerizing agent in the presence of adequate amounts of the four deoxyribonucleoside triphosphates (dATP, dGTP, dCTP, and dTTP) or their analogs as discussed above, in a reaction medium comprised of the appropriate salts, metal cations, and pH buffering system. Suitable polymerizing agents are enzymes known to catalyze primer- and template-dependent DNA synthesis and preferably possess the 5' to 3' nuclease activity. Known DNA polymerases include *E. coli* DNA polymerase I, *Thermus thermophilus* (Tth) DNA polymerase, *Bacillus stearothermophilus* DNA polymerase, *Thermococcus litoralis* DNA polymerase and *Thermus aquaticus* (Taq) DNA polymerase. The reaction conditions for catalyzing DNA synthesis with these DNA polymerases are well known in the art.

Template-dependent degradation of a primer extension product is catalysed by a 5' exonuclease activity in the presence of a reaction medium comprised of the appropriate salts, metal cations, and pH buffering system. It is preferred that the degradation conditions share the same conditions as the extension conditions, and the 5' exonuclease activity is provided by a DNA polymerase which is used for primer extension. It is preferred that Taq DNA polymerase is used as both polymerizing agent and degradation agent.

Detection or verification of the primer extension and degradation product of the first primer extension may be accomplished by a variety of methods and may be dependent on the source of the label or labels employed. In a preferred method, a real-time PCR is used to monitor the signal generation for each cycle of the reaction. In one embodiment, at least one of the nucleoside triphosphates is labelled, whereby creating and/or degrading the extension product of the first primer generates detectable signals. In a preferred embodiment, the first primer is labelled. The first primer may comprise a single label which is not be located at the 5' end. The first primer can preferably comprise an interactive label pair which may not be located at the 5' end. The first primer may be designed so the first and second labels are in a FRET or a contact quenching relationship; upon degradation of the first primer extension product, a detection signal is generated which may be monitored at each cycle of a PCR amplification. The correlation of detection fluorescence signal with the amount of a target nucleic acid sequence or a mutated nucleotide present in a target sequence can be achieved by degradation of the extension product of the labelled first primer.

To provide a control, a general probe that hybridises to an area outside of the diagnostic region where the variant nucleotide is located can be included in a reaction. This general probe will give the signal measuring the total amplification product, including both the wild type and mutated target sequence. The real time monitoring result from the general probe will provide an indication of the amount of starting material that has been added to the reaction vessel. The detection signal from the first primer specific to the variant nucleotide can be normalised with the detection signal from the general probe, thereby providing accurate quantitative data. However, quantitative data can also be inferred from the end point detection signal, as it has been unexpectedly found that the end point fluorescent signal from the labelled first primer correlates well with the amount of variant nucleotide present in a sample. This may be due to the fact that when the reaction reaches the plateau, the amount of the amplification product is the same or similar in different reaction vessels, and that the ratio of the variant nucleotide and wild type nucleotide is maintained during the amplification. It will be appreciated that this reason, it may not be necessary for a reaction to be monitored each cycle as real-time detection. An end-point reading may be taken instead, and this may be well suited for some applications and for some circumstances. For example, where a real-time detection machine is not available; a fluorescence reader may be used to take the end point data as well as the starting point data.

A method of analysing a biological sample for the presence and/or the amount of mutations or polymorphisms at multiple loci of nucleic acid sequence can be conducted in a single reaction vessel. In accordance with one embodiment, multiple first primers for each mutation or polymorphism and multiple second primers and third primers designed to amplify each region harbouring each mutation or polymorphism are included in a single reaction.

Reagents employed in the methods of the invention can be packaged into diagnostic kits. Diagnostic kits include first primers for each diagnostic region of a target nucleic acid sequence, a terminal nucleotide at the 3' of a first type of the first primers being complementary to a suspected variant nucleotide and a terminal nucleotide at the 3' of second type of the first primer being complementary to the corresponding normal nucleotide, such that in use an extension product of the first primer is synthesized when said terminal nucleotide of the first primer is complementary to the corresponding nucleotide in the target nucleic acid, and subsequently the extension product of the first primer is degraded thereby generating detectable signal, no extension product being synthesized when said terminal nucleotide of the first primer is not complementary to the corresponding nucleotide in the target nucleic acid sequence; and corresponding second and third primer for amplifying a target sequence containing the diagnostic region annealing to the first primer. The kit may also contain other suitably packaged reagents and materials needed for amplification, for example, buffers, dNTPs, and/or polymerizing means, and for detection analysis, as well as instructions for conducting the assay.

Thus certain kits of the invention are those adapted for performance of the methods defined herein—for example including combinations of suitably labelled first (degradable) primers, second (amplification primers) and written instructions for performing any of the methods defined herein. They may further include a polymerase having 5' to 3' exonuclease activity and so on.

The invention will now be further described with reference to the following non-limiting Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

EXAMPLES

Example 1

Figure 6:
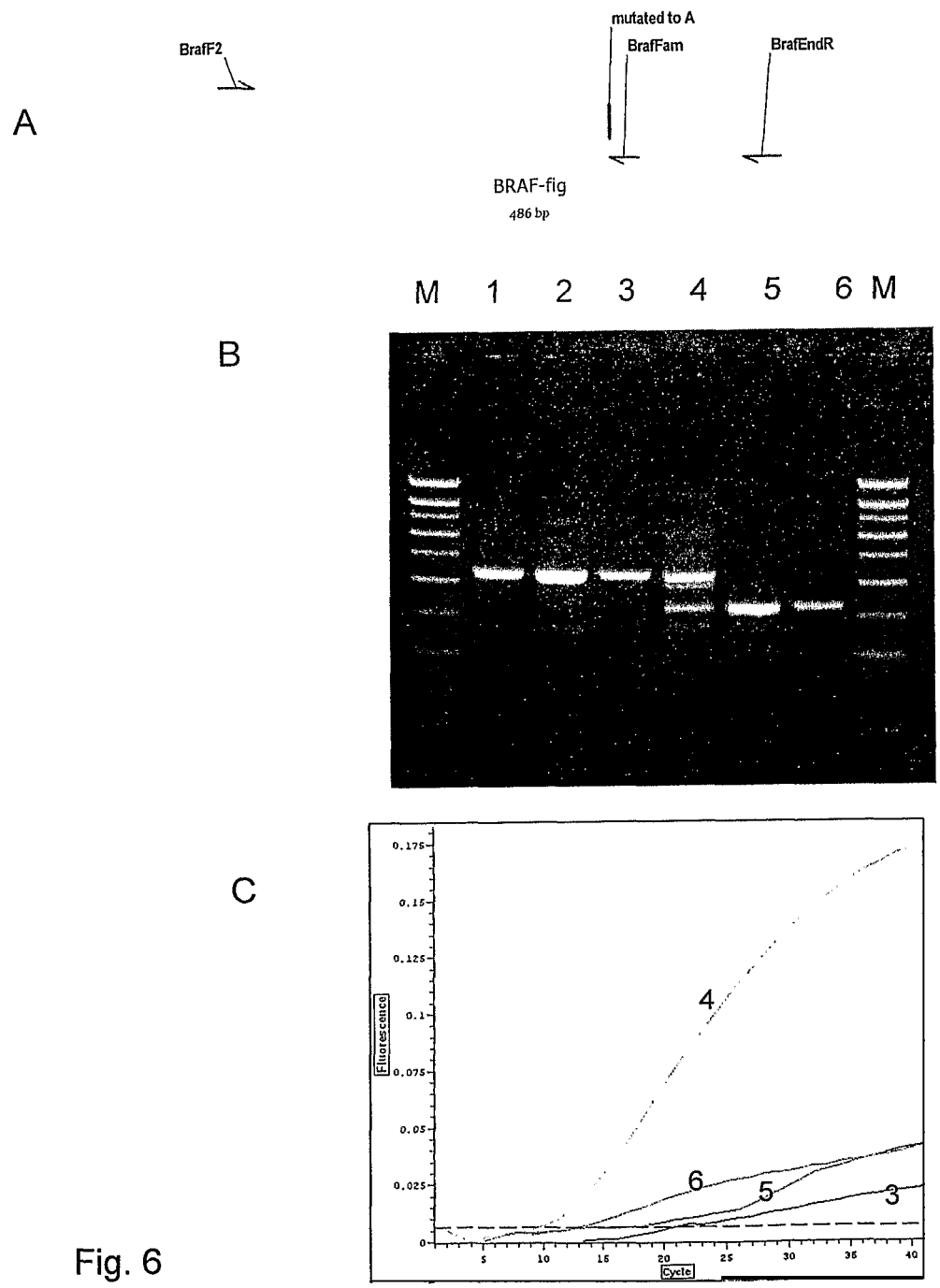
FIG. 6 is an example of an experimental design and the amplification product detected by real-time PCR and in an agarose gel.

All primers used in the subsequent experiments were synthesized by EUROGENTEC, UK. Primers were designed to amplify a target DNA sequence BRAF gene from plasmids comprising a normal BRAF gene fragment and a mutated BRAF gene fragment (harbouring V599E). The sequence of this gene fragment comprises the sequence:

(SEQ ID NO: 1)
Ggaaagcatctcacctcatcctaacacatttcaagccccaaaaatcttaa aagcaggttatataggctaaatagaactaatcattgttttagacatactt attgactctaagaggaaagatgaagtactatgttttaaagaatattatat tacagaattatagaaattagatctcttacctaaactcttcataatgcttg ctctgataggaaatgagatctactgttttcctttacttactacacctca gatatatttcttcatgaagacctcacagtaaaaataggtgattttggtct agctacagtgaaatctcgatggagtgggtcccatcagtttgaacagttgt ctggatccattttgtggatggtaagaattgaggctattttccactgatt aaatttttggccctgagatgctgctgagttactagaaagtcattgaaggt ctcaactatagtattttcatagttcccagtattcac The primer locations and orientations are shown in FIG. 6A. The sequences of the primers are: BrafF2, GGAAAG-CATCTCACCTCATCCTAACAC (SEQ ID NO:2); BrafEndR, GACTTTCTAGTAACTCAGCAGCATCTCAG (SEQ ID NO:3); BrafFam, GGACCCACTCCA1CGAGA2TTCA (SEQ ID NO:4) (1 is dT-Fam, 2 is dT-BHQ1). All nucleic acid sequences are written 5' to 3' unless otherwise stated.

Primers were diluted to a final concentration of 10 μM. Amplification was performed using the following ingredients and conditions: 10×PCR Buffer (ThermoPol Reaction Buffer, NEB) 2.5 μl, 10 mM dNTPs 0.5 μl, each primer, if added, 0.5 μl, Taq DNA polymerase (5 U /μl) 0.25 μl, plasmid DNA 0.5 μl (10⁵ molecules) and water to final volume of 25 μl. Reactions were carried out at 94° C. for 1 min; 40 cycles of 9 sec at 94° C., 15 sec at 57° C., 15 sec at 72° C., 15 sec at 57° C., 15 sec at 72° C. (plate read at this step) on Bio-Rad Chromo4 real-time PCR machine. The primers added in reactions are as follows:

| | Tube number | | | | | |
|---|---|---|---|---|---|---|
| | 1 | 2 | 3 | 4 | 5 | 6 |
| BrafF2 | + | + | + | + | + | + |
| BrafEndR | + | + | + | + | − | − |
| BrafFam | − | − | + | + | + | + |
| Normal DNA | − | + | − | + | − | + |
| Mutated DNA | + | − | + | − | + | − |

After PCR the amplified DNA products were loaded in an agarose gel. The result is shown in FIG. 6B. The real-time PCR result (FIG. 6C) showed that a positive signal is only detected in tube 4 wherein the primers are designed to detect the normal DNA.

Example 2

Amplification primers and probe are: JKR3 ccF2, GAT-GCTCTGAGAAAGGCATTAGAAAG-CATCTTTATTATGGCAGAGAGAASEQ ID NO:5); JKR3, GATGCTCTGAGAAAGGCATTAGA (SEQ ID NO:6); JKFamdR, GTTTTACTTACTCTCGTCTCCAC6GAA (SEQ ID NO:7), in this primer "T" at position 11 is BHQ-1 (dT), "6" is Fam-dR.

Primers are diluted to a final concentration of 10 μM. Amplification is performed using the following ingredients and conditions: 10×PCR Buffer (NEB thermo buffer) 3 μl, 5 μl betain, 10 mM dNTPs 0.5 μl, primer JKR3 1.25 μl, primer JKR3 ccF2 0.5 μl, JKFamdR 1 μl, if added, Taq DNA polymerase (5 U/μl) 0.25 μl, plasmid DNA 0.5 μl (10⁵ molecules) and water to final volume of 25 μl. Reactions are carried out at 94° C. for 1 min; 40 cycles of 15 sec at 95° C., 18 sec at 61° C., 18 sec at 54° C., 18 sec at 72° C., 20 sec at 60° C., 25 sec at 72° C., and 30 sec at 72° C. (data being collected at each temperature) on a Stratagene MX3005 real-time PCR machine. The plasmid template is a mixture of mutated DNA containing V617F and wild type DNA. The method comprises, amplifying the target nucleic acid sequence by real-time PCR; illuminating the biological sample with light of a 492 nm wavelength that is absorbed by Fam; detecting the fluorescence emission of the said fluorophore and monitoring temperature dependent fluorescence from said fluorophore.

The denatured JKR3 ccF2 primer extension product forms a stem-loop structure under annealing condition. The R3 primer is unable to anneal due to the stem-loop structure. The enriching primer JKFamdR anneals to the loop portion and is extended if it anneals to the mutated nucleotide. The extension of primer JKFamdR opens up the stem-loop structure, thereby allowing the R3 primer to anneal and extension. The extension of R3 primer degrades the enriching primer extension product due to the 5' to 3' exonuclease nature of Taq polymerase. The enriching primer extension product also can be displaced if the polymerase has a strand displacement activity. If the enriching primer anneals to the wild type DNA, which contains a nucleotide forming a mismatch with the terminal nucleotide of the primer, the enriching primer is not extended, whereby the stem-loop structure is intact. This results in enriching the DNA containing the mutated nucleotide. The enriching primer comprises labels Fam and BHQ. The degradation of enriching primer extension product gives fluorescence signal. This reaction allows enrichment and detection of the target nucleic acid in the single tube.

Example 3

Amplification primers and probe are: JKR3Hex, AACAGATGCTCTGAGAAAGGCATTAGA (SEQ ID NO:8) (5' end is labeled with HEX); JKR3Dab, CCTTTCTCAGAGCATCTGTT (SEQ ID NO:9) (3' end is labeled with DABCYL); JKF7, GTATGATGAGCAAGCTTTCTCACAA (SEQ ID NO:10).

Primers are diluted to a final concentration of 10 μM. Amplification is performed using the following ingredients and conditions: 10×PCR Buffer (NEB thermo buffer) 3.5 μl, 5 μl betaine, 10 mM dNTPs 0.5 μl, primer JKF7 0.5 μl, primer JKR3Hex 0.75 μl, JKR3Dab 1.25 μl, JKFamdR 1 μl, if added, Taq DNA polymerase (5 U/μl) 0.25 μl, plasmid DNA 0.5 μl (10⁵ molecules) and water to final volume of 25 μl. Reactions are carried out 50 cycles of 15 sec at 95° C., 15 sec at 54° C., 15 sec at 68° C., 15 sec at 59° C., 15 sec at 50° C., 25 sec at 63° C. (data being collected at each temperature) on Stratagene MX3005 real-time PCR machine. The plasmid template is a mixture of mutated DNA containing V617F and wild type DNA. Amplifying of the target nucleic acid sequence is achieved by real-time PCR method.

Primer JKFamdR is the first primer serving as detection primer. Primer JKR3Hex is the second primer serving as one of the amplification primers. Primer JKF7 is the third primer serving as one of the amplification primers. The oligo JKR3Dab is a complement oligo which is complementary to the JKR3Hex. The labels on JKR3Hex and JKR3Dab are in contact quenching relationship when the two oligos hybridise to each other. When the target is present, the primer JKR3Hex preferably hybridises to the target sequence rather than the complement oligo JAR3Dab as it comprises extra nucleotides complementary to the target sequence. The Hex signal indicates that the target is successfully amplified, which can serve as a control. The Fam signal indicates that there is variant nucleotide present in the target, and the level of the Fam signal is correlated with the amount of variant nucleotide present in the target. Apart from probe design here, any probe capable of binding to the amplified product can serve as control for the successful amplification of the target sequence.

Example 4

A first primer also the blocking primer BrafFamWTB having a sequence GGA*C*C*C*A*C*T*CCA*T*C*G*AGA6TTC*A (SEQ ID NO:11) (where "*" is phosphorothioate linkage, "6" is dR-biotin) was designed. The phosphorothioate linkage modifications make the primer resistant to nuclease cleavage. When this primer is used in the reaction, its extension strand is not degraded, thereby blocking the extension initiated from the upstream primer.

The invention claimed is:

1. A method for detecting the presence or absence or amount of a target nucleic acid or at least one variant nucleotide in one or more target nucleic acids contained in a sample, said method comprising:
(a) treating the sample with a first oligonucleotide primer for a first region of a target nucleic acid sequence under hybridisation conditions,
wherein the nucleotide sequence of said first primer is such that it is substantially complementary to said first region of the target nucleic acid such as to anneal thereto thereby creating a mixture of duplexes comprising the first oligonucleotide primer annealed to the target nucleic,
and wherein said first region is a diagnostic portion comprising a suspected variant nucleotide, and wherein a nucleotide at, or within 1, 2, or 3 nucleotides of, the 3' terminus is complementary to the suspected variant nucleotide such that when the first primer anneals to the target region containing the suspected variant nucleotide, the annealed first primer is extendable, and wherein when the first primer anneals to the target region containing the normal nucleotide, the annealed first primer is non-extendable;
(b) maintaining the mixture of step (a) under extension conditions, which comprise appropriate nucleoside triphosphates and a nucleic acid polymerase to extend the annealed first primer, if extendable, to synthesize an extension product of the first primer; and
(c) maintaining the mixture of step (b) under degradation conditions such that if an extension product of the first primer is present, this is degraded under the degradation conditions, thereby generating detectable signals which are indicative of the presence and\or amount of the target nucleic acid or the variant nucleotide in the target nucleic acid,
and if no extension product of the first primer is generated, no degradation of the extension product of the first primer occurs under the degradation conditions, thereby no detectable signals are generated, which is indicative of the absence of the target nucleic acid or the variant nucleotide in the target nucleic acid,
wherein said degradation conditions comprise an exonuclease activity, and wherein
(i) at least one of the said nucleoside triphosphates is labelled, and\or
(ii) the first primer is labelled,
in each case such that degrading the extension product of the first primer generates detectable signals from said label.

2. A method according to claim 1, wherein the 3' terminal nucleotide of said first primer is complementary to a suspected variant nucleotide.

3. A method according to claim 1, wherein said suspected variant nucleotide is a SNP or mutated nucleotide(s).

4. A method according to claim 1, wherein said degradation is carried out as template-dependent degradation.

5. A method according to claim 1, wherein said nuclease activity is 5' to 3' exonuclease activity.

6. A method according to claim 5, wherein said 5' to 3' exonuclease activity is provided by a DNA polymerase.

7. A method according to claim 6, wherein said DNA polymerase is the same as used in step (b).

8. A method according to claim 6, wherein said DNA polymerase is Taq DNA polymerase.

9. A method according to claim 1, wherein step (a) comprises treating the sample with a first oligonucleotide primer for a first region of a target nucleic acid sequence and a second oligonucleotide primer for a second region of the same strand of target nucleic acid sequence to create a mixture of duplexes comprising the first and second oligonucleotide primers annealed to the target nucleic acid under hybridisation conditions,
wherein the nucleotide sequence of said first primer is such that it is substantially complementary to said first region of the target nucleic acid,
and wherein the nucleotide sequence of said second primer is such that it is substantially complementary to said second region of the target nucleic acid,
and wherein the second region of the target nucleic acid is located 3' of the first region of the target nucleic acid.

10. A method according to claim 9, wherein step (b) further comprises extending the annealed first and second primer, if extendable, to synthesize extension products of the first and second primers under extension conditions, which comprise appropriate nucleoside triphosphates and a nucleic acid polymerase, wherein in step (c) the degradation of the extension product of the first primer occurs as a result of the extension of the second primer.

11. A method according to claim 1, wherein step (a) further comprises treating the sample with at least two types of the first oligonucleotide primer for the first region of a target nucleic acid sequence to create a mixture of duplexes comprising the first oligonucleotide primer annealed to the target nucleic acid under hybridisation conditions,
wherein the nucleotide sequence of said first primer is such that it is substantially complementary to said first region of the target nucleic acid,
and wherein a 3 terminal nucleotide of said first type of the first primer is complementary to a suspected variant nucleotide,
and wherein a 3' terminal nucleotide of said second type of the first primer is complementary to the corresponding normal nucleotide,
whereby in step (b) an extension product of the first type of the first primer is synthesized when said first type of the first primer anneals to the first region containing the suspected variant nucleotide in the target nucleic acid sequence whereas no extension product is synthesized when said first type of the first primer anneals to the first region containing corresponding normal nucleotide in the target nucleic acid,
and whereby in step (b) an extension product of the second type of the first primer is synthesized when said second type of the first primer anneals to the first region containing the normal nucleotide in the target nucleic acid sequence, whereas no extension product is synthesized when said second type of the first primer anneals to the first region containing corresponding variant nucleotide in the target nucleic acid.

12. A method according to claim 11, wherein either (i) said first type and second type of the first primers are degradable, or (ii) said second type of the first primer is non-degradable, wherein the second type of the first primer comprises modified nucleotides or modified linkages or non-nucleotides, whereby the extension product of the second type of the first primers blocks the extension initiated from the second primer, thereby enriching the target nucleic acid containing the suspected variant nucleotide.

13. A method according to claim 1, wherein steps (a), (b) and (c) are parts of a PCR reaction, which comprises:
  treating the sample under denaturing conditions to separate the primer extension product from its template where such extension product is formed;
  contacting single strands produced above, either together or sequentially, with appropriate nucleoside triphosphates, a nucleic acid polymerase having 5' to 3' nuclease activity, one or more types of first primer, a second primer and a third primer, wherein
the or each first primer is labelled such that degrading the extension product of the first primer generates detectable signals,
  whereby, where possible, further extension products are synthesized using the single strands produced above as template,
  and wherein degradation of the extension product of the first primer is achieved by said nucleic acid polymerase having 5 to 3' nuclease activity occurs during extension of the second primer,
  and wherein said third primer comprises a sequence substantially complementary to the extension product of the second primer;
repeating the above steps a sufficient number of times to result in detectable signals from the degradation of the or each first primer in the presence of the of the target nucleic acid or the variant nucleotide in the target nucleic acid.

14. A method according to claim 13, wherein said first primer is labelled not at the 5' terminus.

15. A method according to claim 14, wherein said first primer is labelled at least 3, 6 or 9 nucleotides away from the 5' terminus.

16. A method according to claim 13, wherein said first primer comprises first and second labels which are interactive pair.

17. A method according claim 1, wherein said first primer comprises
  (a) a priming portion which is complementary to the first region of the target nucleic acid sequence, and further comprises
  (b) a first tail of non-nucleic acids or a sequence of nucleotides at the 5' end which is non-complementary to the target nucleic acid sequence, and optionally further comprises
  (c) a second tail of non-nucleic acids or a sequence of nucleotides which is linked to said first tail and is substantially complementary to the target nucleic acid sequence which is adjacent to the region complementary to the priming portion of the first primer.

18. A method according to claim 17, wherein said first primer comprises a double-stranded portion at the first tail, wherein a tail complement oligonucleotide complementary to the first tail is annealed to the first tail sequence,
  wherein said first primer is labelled with a first label and said tail complement oligonucleotide is labelled with a second label,
  and wherein said first label and second label are interactive pair.

19. A method according to claim 1, wherein said first primer comprises a region capable of forming a double-stranded duplex with a first complement oligonucleotide which is capable of hybridising to the first primer,
  wherein the first primer is capable of hybridising to the target nucleic acid with greater affinity than to the first complement oligonucleotide,
  and wherein the first primer and the first complement oligonucleotide are each labelled with one member of an interactive label pair consisting of a first label and a second label,
  such that upon amplification of the target nucleic acid, the first primer hybridizes to the amplified product of the target nucleotide in preference to the first complement oligonucleotide, and the interactive label pair are thereby separated.

20. A method according to claim 11, wherein said second primer comprises a region capable of forming a double-stranded duplex with a second complement oligonucleotide which is capable of hybridising to the second primer,
  wherein the second primer is capable of hybridising to the target nucleic acid with greater affinity than to the second complement oligonucleotide,
  and wherein the primer and its complement oligonucleotide are each labelled with one member of an interactive label pair consisting of a first label and a second label,
  such that upon amplification of the target nucleic acid, the primer hybridizes to the amplified product of the target nucleotide in preference to the complement oligonucleotide, and the interactive label pair are thereby separated.

21. A method according to claim 13, wherein said third primer comprises a region capable of forming a double-stranded duplex with a third complement oligonucleotide which is capable of hybridising to the third primer,
  wherein the third primer is capable of hybridising to the target nucleic acid with greater affinity than to the third complement oligonucleotide,
  and wherein the primer and its complement oligonucleotide are each labelled with one member of an interactive label pair consisting of a first label and a second label,
  such that upon amplification of the target nucleic acid, the primer hybridizes to the amplified product of the target nucleotide in preference to the complement oligonucleotide, and the interactive label pair are thereby separated.

22. A method according to claim 16, wherein said first label and label are each a fluorophore and a quencher.

23. A method according to claim 12, wherein said two types of the first primers are attached with different labels which generate distinguishable signals during degradation of the extension products of the first primers, if both types of the first primer are extended.

* * * * *